(12) United States Patent
Nguyen et al.

(10) Patent No.: US 11,795,044 B2
(45) Date of Patent: Oct. 24, 2023

(54) AMPOULE BREAKER FOR A BIOLOGICAL INDICATOR

(71) Applicant: Advanced Sterilization Products, Inc., Irvine, CA (US)

(72) Inventors: Nick N. Nguyen, Silverado, CA (US); Samuel J. Rhodes, Los Angeles, CA (US); Mark J. Lubong, Irvine, CA (US); Derrick C. Tan, Yorba Linda, CA (US)

(73) Assignee: Advanced Sterilization Products, Inc., Irvine, CA (US)

( * ) Notice: Subject to any disclaimer, the term of this patent is extended or adjusted under 35 U.S.C. 154(b) by 0 days.

(21) Appl. No.: 17/773,821

(22) PCT Filed: Nov. 4, 2021

(86) PCT No.: PCT/IB2021/060235
§ 371 (c)(1),
(2) Date: May 2, 2022

(87) PCT Pub. No.: WO2022/101750
PCT Pub. Date: May 19, 2022

(65) Prior Publication Data
US 2022/0411247 A1    Dec. 29, 2022

Related U.S. Application Data

(60) Provisional application No. 63/112,069, filed on Nov. 10, 2020.

(51) Int. Cl.
*B67B 7/92*    (2006.01)

(52) U.S. Cl.
CPC ..................... *B67B 7/92* (2013.01)

(58) Field of Classification Search
CPC ......... B27B 7/92; B27B 17/8833; A61L 2/28; B01F 35/7131; B01F 35/75425;
(Continued)

(56) References Cited

U.S. PATENT DOCUMENTS 2,447,988 A * 8/1948 Pierson ..................... B67B 7/92
451/540
3,346,464 A   10/1967 Ernst
(Continued)

FOREIGN PATENT DOCUMENTS

CA    738687 A    7/1966
CA    823163 A    9/1969
(Continued)

OTHER PUBLICATIONS

NAMSA, Self-Contained Biological Indicators for Monitoring Steam, Northwood, Ohio, 2015.
(Continued)

*Primary Examiner* — Ghassem Alie
(74) *Attorney, Agent, or Firm* — Lerner David LLP

(57) ABSTRACT

A device for breaking an ampoule of a biological indicator includes: a main body; a pivoting body attached to the main body at a main pivot point; a receiving area in the main body and configured to receive the biological indicator; a pressing surface inside the pivoting body; and a compressing element including a compressing surface, the compressing surface being operable between a first position and a second position located in the receiving area.

13 Claims, 9 Drawing Sheets

(58) Field of Classification Search
CPC ........ B65D 47/36; B65D 1/0238; B65D 1/00;
B65D 1/0253; A61J 1/06; Y10T 225/30;
Y10T 225/213; Y10T 225/208; Y10T 225/214
USPC ..... 225/1, 93, 97, 103; 241/34, 96, 96.5, 99, 241/105; 435/29
See application file for complete search history.

(56) References Cited

U.S. PATENT DOCUMENTS

| | | |
|---|---|---|
| 3,450,319 A | 6/1969 | Ray et al. |
| 3,752,743 A | 8/1973 | Henshilwood |
| 3,948,727 A | 4/1976 | Steiger |
| 4,291,122 A | 9/1981 | Orelski |
| 4,304,869 A | 12/1981 | Dyke |
| 4,528,268 A | 7/1985 | Andersen et al. |
| 4,537,099 A * | 8/1985 | Oster ............ C03B 33/12 81/355 |
| 4,546,086 A | 10/1985 | Hounsell |
| 4,637,139 A * | 1/1987 | Chen ............ B67B 7/92 241/606 |
| 4,717,661 A | 1/1988 | McCormick et al. |
| 4,732,850 A | 3/1988 | Brown et al. |
| 4,741,437 A | 5/1988 | Gorski et al. |
| 4,839,291 A | 6/1989 | Welsh et al. |
| 4,883,641 A | 11/1989 | Wicks et al. |
| 4,885,253 A | 12/1989 | Kralovic |
| 5,028,543 A | 7/1991 | Finch et al. |
| 5,073,488 A | 12/1991 | Matner et al. |
| 5,167,923 A | 12/1992 | Van Iperen |
| 5,223,401 A | 6/1993 | Foltz et al. |
| 5,252,484 A | 10/1993 | Matner et al. |
| 5,293,816 A * | 3/1994 | Musumeci, Sr. ....... B30B 9/321 100/291 |
| 5,362,654 A | 11/1994 | Pouletty |
| 5,405,580 A | 4/1995 | Palmer |
| 5,415,994 A | 5/1995 | Imrich et al. |
| 5,418,167 A | 5/1995 | Matner et al. |
| 5,482,171 A | 1/1996 | Palmer |
| 5,516,648 A | 5/1996 | Malchesky et al. |
| 5,552,320 A | 9/1996 | Smith |
| 5,736,355 A | 4/1998 | Dyke et al. |
| 5,739,004 A | 4/1998 | Woodson |
| 5,750,184 A | 5/1998 | Imburgia |
| 5,759,848 A | 6/1998 | Nagoshi et al. |
| 5,770,393 A | 6/1998 | Dalmasso et al. |
| 5,801,010 A | 9/1998 | Falkowski et al. |
| 5,830,683 A | 11/1998 | Hendricks et al. |
| 5,863,790 A | 1/1999 | Bolea |
| 5,866,356 A | 2/1999 | Albert et al. |
| 5,942,438 A | 8/1999 | Antonoplos et al. |
| 6,218,189 B1 | 4/2001 | Antonoplos et al. |
| 6,436,659 B1 | 8/2002 | Hui et al. |
| 6,458,554 B1 | 10/2002 | Hui et al. |
| 6,551,555 B2 | 4/2003 | Antonoplos et al. |
| 6,924,139 B2 | 8/2005 | Eveland et al. |
| 7,091,042 B2 | 8/2006 | Lemus et al. |
| 7,247,482 B2 | 7/2007 | Lemus et al. |
| 7,642,067 B2 | 1/2010 | Song et al. |
| 8,173,388 B2 | 5/2012 | Pasmore et al. |
| 8,173,418 B2 * | 5/2012 | Sestak ............ C12M 37/06 435/31 |
| 8,173,438 B1 | 5/2012 | Putnam et al. |
| 8,765,398 B2 | 7/2014 | Dalmasso |
| 8,840,837 B2 | 9/2014 | Smith et al. |
| 8,915,413 B2 | 12/2014 | Kayser |
| 8,945,837 B2 | 2/2015 | Franciskovich et al. |
| 8,969,029 B2 | 3/2015 | Chandrapati et al. |
| 8,980,622 B2 | 3/2015 | Smith et al. |
| 9,145,573 B2 | 9/2015 | Pederson et al. |
| 9,321,973 B2 | 4/2016 | Marchand et al. |
| 9,322,046 B2 | 4/2016 | Chandrapati et al. |
| 9,525,317 B2 | 12/2016 | Ohashi et al. |
| 9,675,722 B2 | 6/2017 | Ahimou et al. |
| 9,856,124 B2 * | 1/2018 | Mitidieri ............ B67B 7/92 |
| 10,059,977 B2 | 8/2018 | Witcher et al. |
| 10,150,901 B2 | 12/2018 | Boutier et al. |
| 10,561,753 B2 | 2/2020 | Thompson et al. |
| 2004/0197848 A1 | 10/2004 | Behun et al. |
| 2005/0014214 A1 * | 1/2005 | Eveland ............ C12Q 1/04 435/29 |
| 2008/0070272 A1 | 3/2008 | Franciskovich et al. |
| 2009/0068716 A1 | 3/2009 | Hirota et al. |
| 2011/0200992 A1 | 8/2011 | Chandrapati et al. |
| 2012/0149094 A1 | 6/2012 | Smith et al. |
| 2012/0156090 A1 | 6/2012 | Dane et al. |
| 2013/0210048 A1 | 8/2013 | Chandrapati et al. |
| 2013/0217107 A1 | 8/2013 | Pederson et al. |
| 2013/0224849 A1 | 8/2013 | Chandrapati et al. |
| 2013/0273594 A1 | 10/2013 | Ahimou et al. |
| 2015/0004682 A1 | 1/2015 | Smith et al. |
| 2015/0167047 A1 | 6/2015 | Smith et al. |
| 2015/0337354 A1 | 11/2015 | Ahimou et al. |
| 2016/0000954 A1 | 1/2016 | Ahimou et al. |
| 2017/0175071 A1 | 6/2017 | Sullivan et al. |
| 2017/0211035 A1 | 7/2017 | Yirava et al. |
| 2017/0253845 A1 | 9/2017 | Amin |
| 2018/0015193 A1 | 1/2018 | Swaminathan et al. |
| 2018/0071421 A1 | 3/2018 | Fang et al. |
| 2018/0187142 A1 | 7/2018 | Truong |
| 2018/0237821 A1 | 8/2018 | Fryer |
| 2019/0002951 A1 | 1/2019 | Fryer et al. |
| 2019/0106725 A1 | 4/2019 | Cregger et al. |
| 2019/0106726 A1 | 4/2019 | Cregger et al. |
| 2019/0169672 A1 | 6/2019 | Fryer et al. |
| 2020/0165658 A1 | 5/2020 | Bala et al. |
| 2021/0147784 A1 | 5/2021 | Amin |

FOREIGN PATENT DOCUMENTS

| | | |
|---|---|---|
| CA | 1 182 729 A | 2/1985 |
| CN | 1853734 A | 11/2006 |
| CN | 201453688 U | 5/2010 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 106966348 A | 7/2017 |
| CN | 206473580 U | 9/2017 |
| CN | 206970617 U | 2/2018 |
| EP | 0 152 298 A2 | 8/1985 |
| EP | 1032822 B1 | 5/2003 |
| EP | 2968634 B1 | 12/2016 |
| FR | 2708287 B1 | 10/1995 |
| GB | 1055387 A | 1/1967 |
| IN | 201747012748 A | 4/2017 |
| IN | 201714046902 A | 7/2018 |
| JP | H10201466 A | 8/1998 |
| JP | H11196893 A | 7/1999 |
| JP | 2017123976 A | 7/2017 |
| JP | 2018201397 A | 12/2018 |
| RU | 129814 U1 | 7/2013 |
| RU | 143648 U1 | 7/2014 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2008/106327 A2 | 9/2008 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018/025207 A1 | 2/2018 |
| WO | 2018/160449 A1 | 9/2018 |

(56) References Cited

FOREIGN PATENT DOCUMENTS

| WO | 2020/136463 A1 | 7/2020 |
|----|----------------|--------|
| WO | 2021/053627 A1 | 3/2021 |

OTHER PUBLICATIONS

Anonymous, 3M™ Attest™ 1292E Rapid Readout Biological Indicator, Internet Article, Jan. 1, 1999, http://multimedia.3m.com/mws/mediawebserver?mwsId=SSSSSu7zK1fslxtU48_el8mGev7qe17zHvTSevTSeSSSSSS--&fn=Rapid_Readout_Profile_1292E.pdf.

Chinese First Office Action and Search Report for Chinese Patent Application No. 201810004516.1 dated Aug. 3, 2020 and English translation.

PCT Notification of Transmittal of the International Search Report and the Written Opinion of the International Searching Authority, or the Declaration for International Application No. PCT/IB2020/058750 dated Nov. 27, 2020, 1 page.

PCT Written Opinion of the International Searching Authority for International Application No. PCT/IB2020/058750 dated Nov. 27, 2020, 6 pages.

PCT International Search Report for International Application No. PCT/IB2020/058750 dated Nov. 27, 2020, 6 pages.

Russian Search Report for Registration No. 2017145872/04(078515) dated Dec. 26, 2017, date of valid search completion: Jun. 10, 2021, 2 pages.

PCT Notification of Transmittal of the International Search Report and the Written Opinion of the International Searching Authority, or the Declaration for International Application No. PCT/IB2021/060235, dated Feb. 18, 2022, 9 pages.

Verify SCBI HP Activator, Part No. LCB004, Steris Product No. LCB004 is a Verify Self-Contained Biological Indicator HP, 2 pages.

* cited by examiner

AMPOULE BREAKER FOR A BIOLOGICAL INDICATOR

CROSS-REFERENCE TO RELATED APPLICATIONS

The present application is a U.S. National Phase Application of International Application No. PCT/IB2021/060235, filed Nov. 4, 2021 which claims priority to U.S. Provisional Patent Application No. 63/112,069, filed Nov. 10, 2020. The entire contents of these applications are incorporated by reference herein in their entirety.

FIELD

The subject matter disclosed herein relates to biological indicators and, in particular to devices to break a biological indicator ampoule.

BACKGROUND

Medical devices are typically sterilized before use. Biological sterilization indicators, or biological indicators, are used to determine if a sterilization cycle has been efficacious. Typically, a sterilized medical device is not itself checked for contaminating organisms because such an activity could introduce other contaminating organisms to the medical device. An indirect check for contamination is performed using a biological indicator. A biological indicator is a device that is placed alongside or in proximity to a medical device being subjected to a sterilization cycle such that the biological indicator is subject to the same sterilization cycle as the medical device. For example, a biological indicator containing a predetermined quantity of microorganisms possessing known resistance to the sterilant can be placed into a sterilization chamber with the medical device. After the sterilization cycle is complete, the microorganisms in the biological indicator can be cultured to determine whether any of the microorganisms survived the sterilization.

Self-contained biological indicators contain a frangible vial, or ampoule, that contains a growth media and a housing that contains a quantity of microorganisms. The ampoule is located in the housing and separates the growth media from the microorganisms. After the sterilization cycle, the ampoule is broken to release the growth media into the housing so that it contacts the microorganisms. Examples of self-contained biological indicators have a housing in which one portion of the housing telescopes into another portion of the housing, which places pressure on, and breaks, the ampoule. Various methods are used to compress the housing with sufficient force to break the ampoule.

SUMMARY OF THE DISCLOSURE

A device for breaking an ampoule of a biological indicator comprises a main body, a pivoting body attached to the main body at a main pivot point, a receiving area in the main body configured to receive the biological indicator, a pressing surface inside the pivoting body, and a compressing element including a compressing surface. The compressing surface may be operable between a first position and a second position located in the receiving area. A compression pivot point may also be provided and the compressing element may be attached to the pivoting body. The device may also include an urging member located between the main body and the compressing element that urges the compressing element against the pressing surface.

A device for breaking an ampoule of a biological indicator may alternatively comprise a main body, a pivoting body attached to the main body at a main pivot point, the pivoting body being pivotable between a rest position and a biological indicator compressing position, a receiving area configured to receive a biological indicator. The receiving area may extend in a longitudinal direction and having an end wall at one end of the receiving area in the longitudinal direction. The device may also include an angled surface inside the pivoting body, that is positioned at a positive angle relative to the longitudinal direction of the receiving area, such that the angled surface is closer to the end wall in the biological indicator compressing position than in the rest position. In this device, pivoting the pivoting body relative to the main body about the main pivot point causes the angled surface to move relative to the end wall.

A device for breaking an ampoule of a biological indicator may alternatively comprise a main body, a pivoting body attached to the main body at a pivot point, a first receiving area in the pivoting body configured to receive a first portion of a biological indicator, a retaining surface inside the pivoting body configured to receive an end of the biological indicator, and a pressing surface that moves with the main body and is located opposite the first receiving area, such that the pressing surface is closer to the retaining surface in the compressed position than in the rest position.

The device, in any of its embodiments, may assist a user to break an ampoule of a biological indicator to activate the biological indicator.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
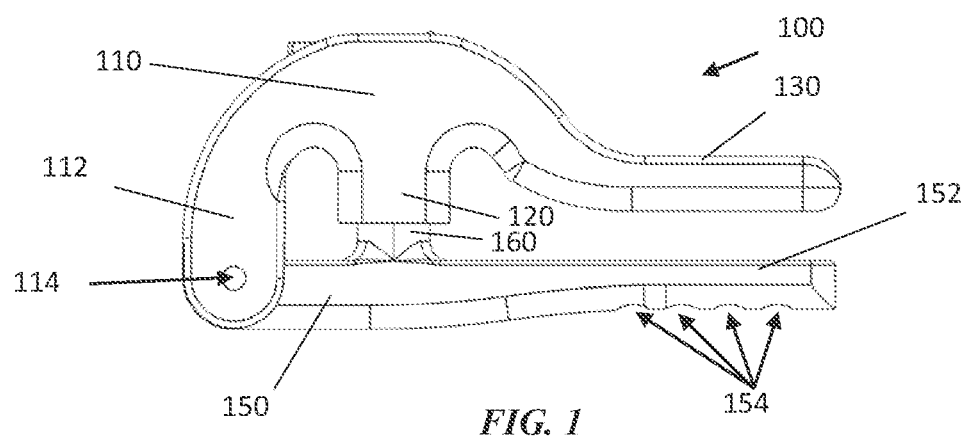
FIG. 1 depicts a side view of an exemplary ampoule breaker.

FIG. 1 shows an exemplary ampoule breaker 100 that is used for breaking an ampoule inside a biological indicator Ampoule breaker 100 has a main body 110 and a pivoting body 150. Pivoting body 150 is attached to main body 110 at a pivot point. Main body 110 has a hole 114 in each of two connection portions 112 that extend downward from main body 110. Pivoting body 150 comprises a pivot handle 152 that may include indentations 154 to receive fingers of a user. Main body 110 has a main handle 130 that extends substantially parallel to pivot handle 150. In use, the user grips both pivot handle 152 and main handle 130 and squeezes them towards each other. A receiving area such as biological indicator holder 160 extends upwardly from pivoting body 150. Biological indicator holder 160 supports a biological indicator while it is compressed by ampoule breaker 100. A sheath 120 extends downwardly from main body 110 and surrounds biological indicator holder 160.

Figure 2:
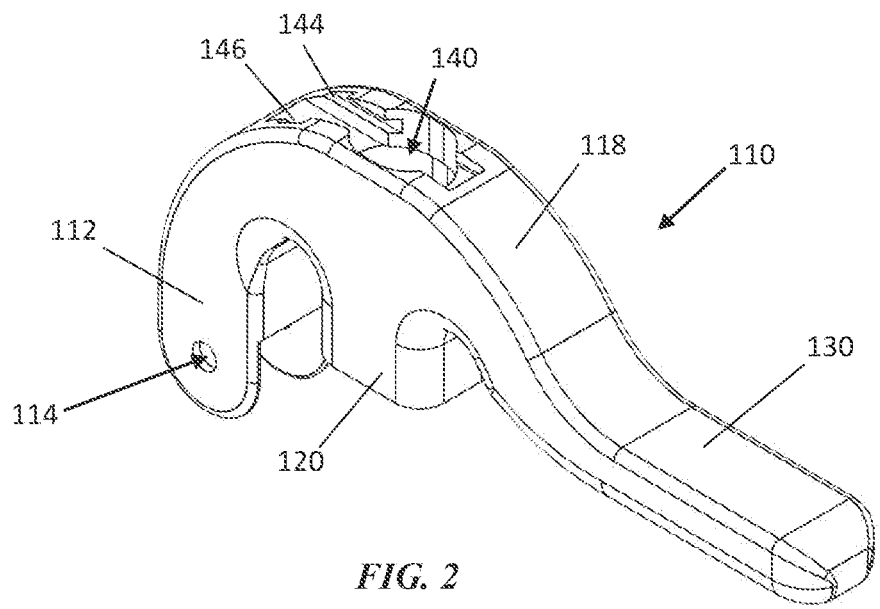
FIG. 2 depicts a perspective view of a main body of the ampoule breaker of FIG. 1.
Figure 3:
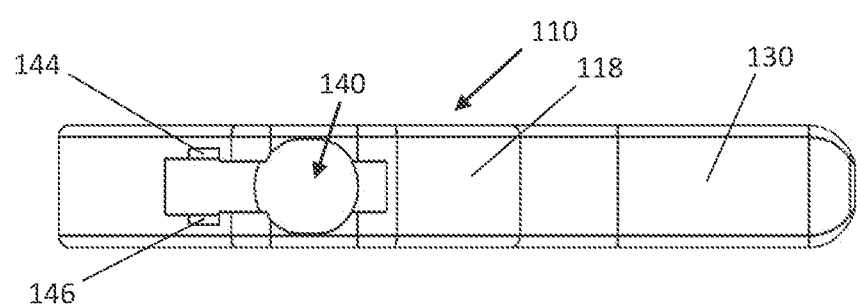
FIG. 3 depicts a top view of the ampoule breaker of FIG. 1.

FIG. 2 is a perspective view of main body 110. As shown in FIG. 2, main body 110 has a receiving area 140 in an upper portion of main body 110. A transition portion 118 extends from the upper portion of main body 110 and transitions smoothly to main handle 130. FIG. 3 is a top view of ampoule breaker 100. As shown in FIGS. 2 and 3, receiving area 140 is circular in shape and extends downwardly through main body 110 and sheath 120. Adjacent to receiving area 140 are two receptacles 144 and 146. Receptacles 144 and 146 are configured to receive a cover 200 (described below) that slides relative to main body 110 to cover receiving area 140. In a closed position, cover 200 covers receiving area 140 and any biological indicator that is in receiving area 140. In an open position, cover 200 allows a biological indicator to be inserted into receiving area 140.

Figure 4:
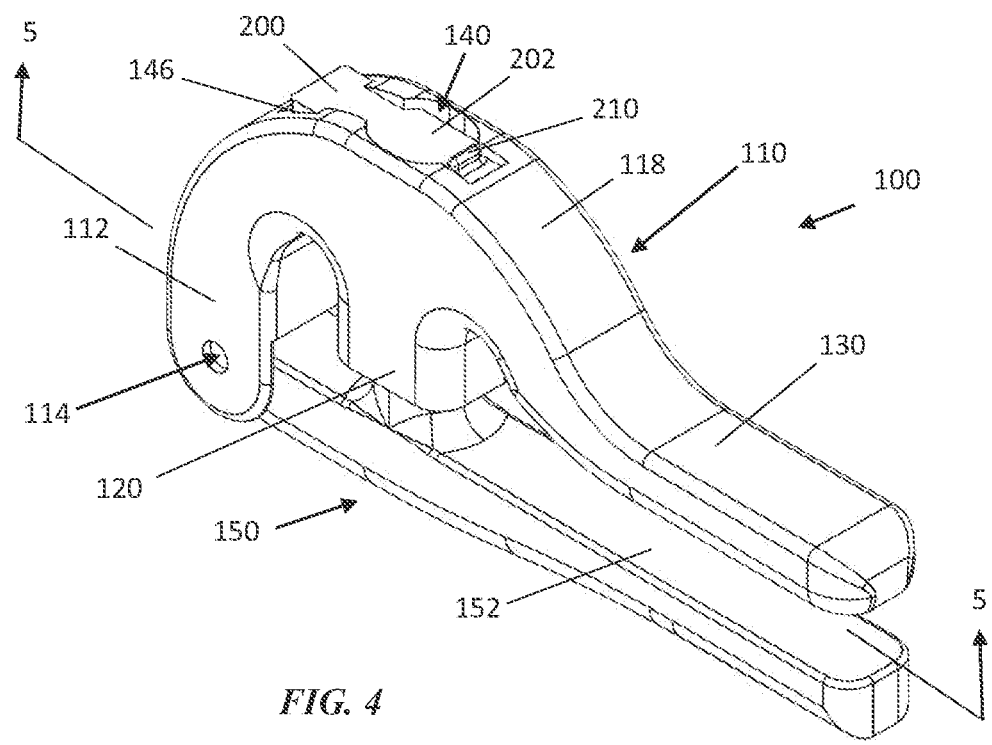
FIG. 4 depicts a perspective view of the ampoule breaker of FIG. 1.

FIG. 4 is a perspective view of ampoule breaker 100 with cover 200 in the closed position. An upper surface 202 of cover 200 can be seen in FIG. 4. In use, cover 200 is in an open position where receiving area 140 is open to allow insertion of a biological indicator into receiving area 140. After the biological indicator is completely inserted into receiving area 140, cover 200 slides from the open position to a closed position to cover the biological indicator. FIG. 4 shows a gripping portion 210 that extends from upper surface 202 of cover 200. Gripping portion 210 facilitates the movement of cover 200 by the user between the open position and the closed position.

Figure 5:
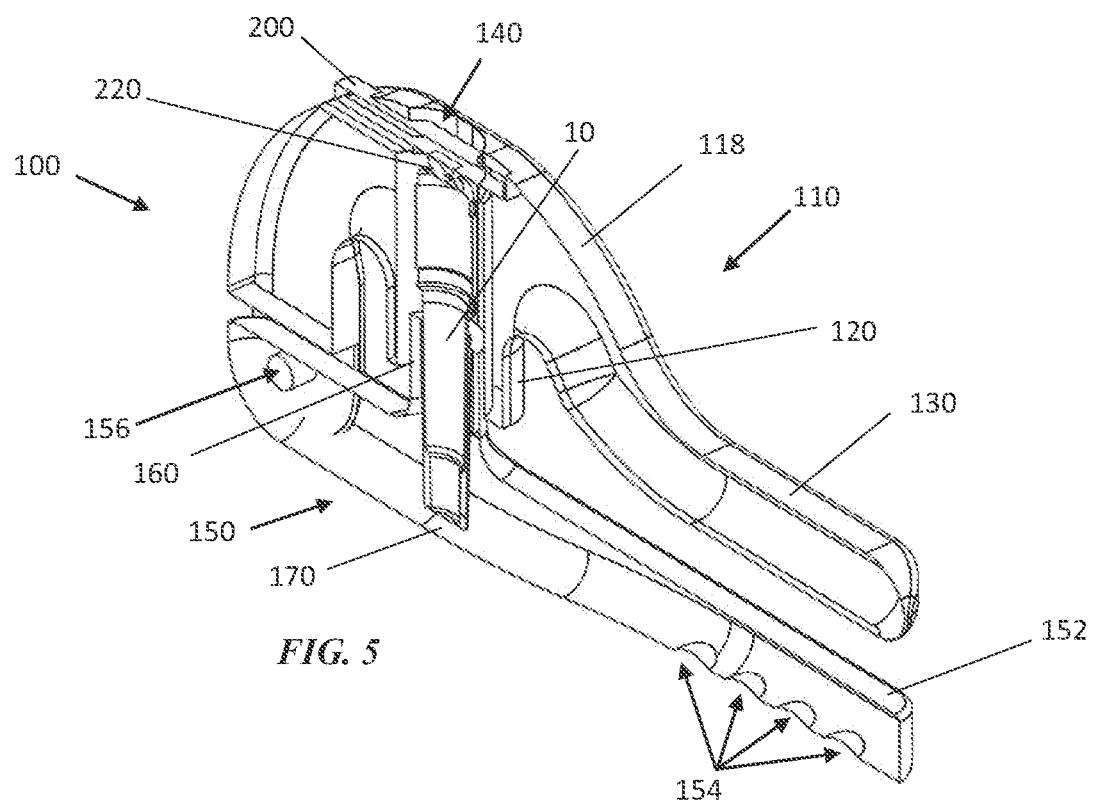
FIG. 5 depicts a perspective sectional view of the ampoule breaker of FIG. 1.

FIG. 5 is a sectional view of ampoule breaker 100 taken along section line 5-5 in FIG. 4. FIG. 5 shows a biological indicator 10 in position in receiving area 140. As shown in FIG. 5, a pressing surface 220 on a lower surface 204 of cover 200 contacts a top end of biological indicator 10 and the bottom end of biological indicator 10 contacts a retaining surface 170 of pivoting body 150. When main handle 130 and pivot handle 152 are pressed toward each other, moving from a rest position to a compressed position, pressing surface 220 contacts a top end of biological indicator 10 and pushes it downward while the bottom end of biological indicator 10 is prevented from moving by retaining surface 170 in pivot handle 152. In this manner, an ampoule inside biological indicator 10 is broken. Also shown in FIG. 5, is a hole 156 that aligns with holes 114 in main body 110. A pin 390 (similar to pin 390 in FIG. 10) extends through one hole 114, hole 156, and the other hole 114 and is a pivoting point about which pivoting body 150 moves relative to main body 110.

Figure 6:
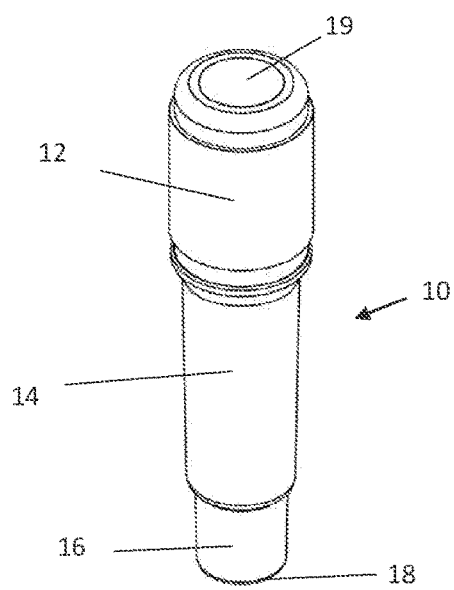
FIG. 6 depicts a biological indicator for use with an ampoule breaker.
Figure 15:
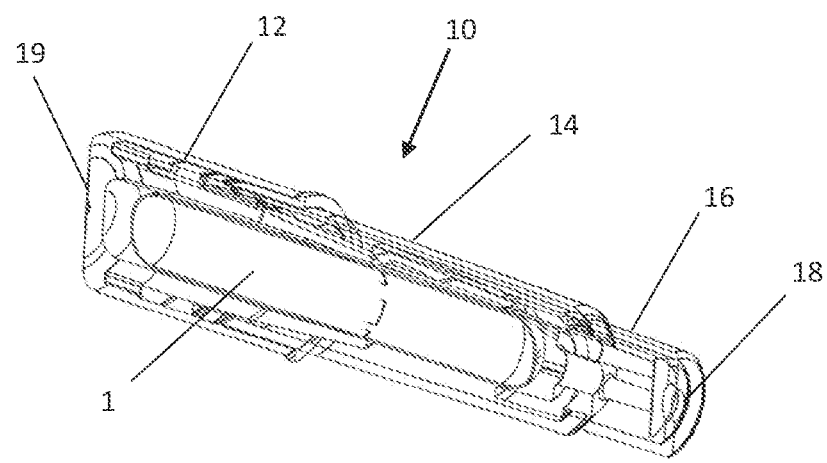
FIG. 15 depicts a sectional view of the biological indicator of FIG. 6.

FIG. 6 shows an example of biological indicator 10 which has a first section 12, a second section 14, a third section 16, a lower end 18, and an upper end 19. FIG. 15 shows a sectional view of biological indicator 10 showing an ampoule 1 located inside first section 12 and second section 14. As lower end 18 and upper end 19 are pressed toward each other, second section 14 slides inside first section 12 causing ampoule 1 to be compressed to the point of breaking. In other examples, biological indicator 10 compresses ampoule 1 in different manners.

Figure 7:
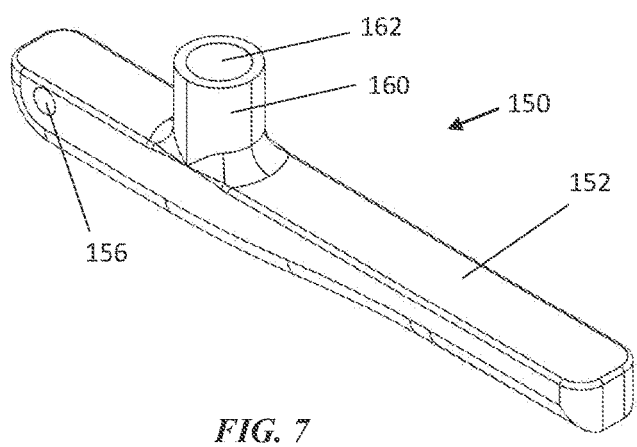
FIG. 7 depicts a perspective view of a pivoting body of the ampoule breaker of FIG. 1.
Figure 8:
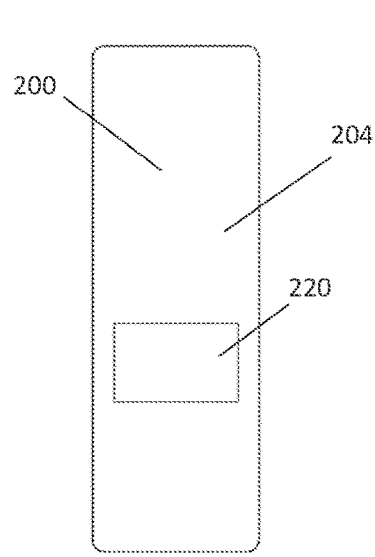
FIG. 8 depicts a bottom view of a receiving area cover of the ampoule breaker of FIG. 1.
Figure 9:
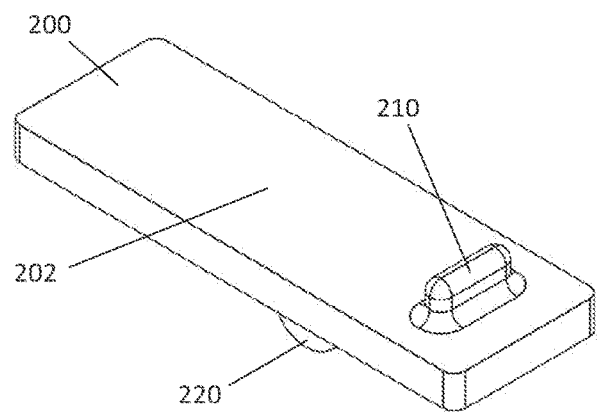
FIG. 9 depicts a perspective view of a receiving area cover of the ampoule breaker of FIG. 1.

FIG. 7 shows pivoting body 150 having biological indicator holder 160 extending upward and having a receiving area 162 for receiving biological indicator 10. FIGS. 8 and 9 show cover 200. As shown in FIG. 8, pressing surface 220 extends from lower surface 204 of cover 200. As shown in FIG. 9, gripping portion 210 extends upward from upper surface 202 of cover 200.

Figure 10:
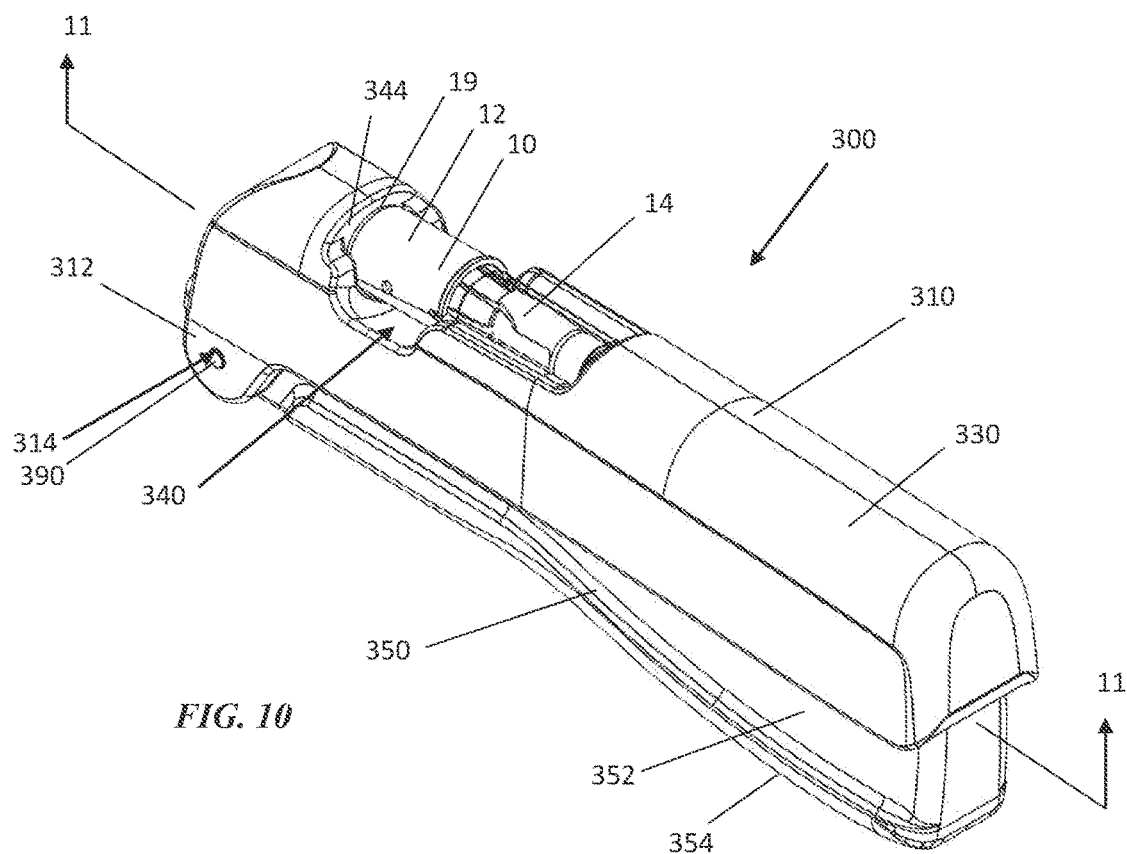
FIG. 10 depicts a perspective view of an exemplary ampoule breaker.

FIG. 10 shows an exemplary ampoule breaker 300 that is used for breaking an ampoule inside biological indicator 10. Ampoule breaker 300 has a main body 310 and a pivoting body 350. Pivoting body 350 is attached to main body 310 at a pivot point by a pin 390. Main body 310 as a hole 314 in each of two connection portions 312 that extend downward from main body 310. Pivoting body 350 a pivot handle 352 that has a grip section 354 to receive fingers of a user. Main body 310 has a main handle 330 that extends substantially parallel to pivot handle 350. In use, the user grips both pivot handle 352 and main handle 330 and squeezes them towards each other. Main body 310 has a receiving area 340 located in an upper region of main body 310. Receiving area 340 is configured to receive biological indicator 10 as shown in FIG. 10. Receiving area 340 has an end wall 344 that prevents upper end 19 of biological indicator 10 from moving when ampoule breaker 300 is operated. Receiving area 340 has two lateral stops 348 that prevent upper end 19 of biological indicator 10 from moving laterally when ampoule breaker 300 is operated.

Figure 11:
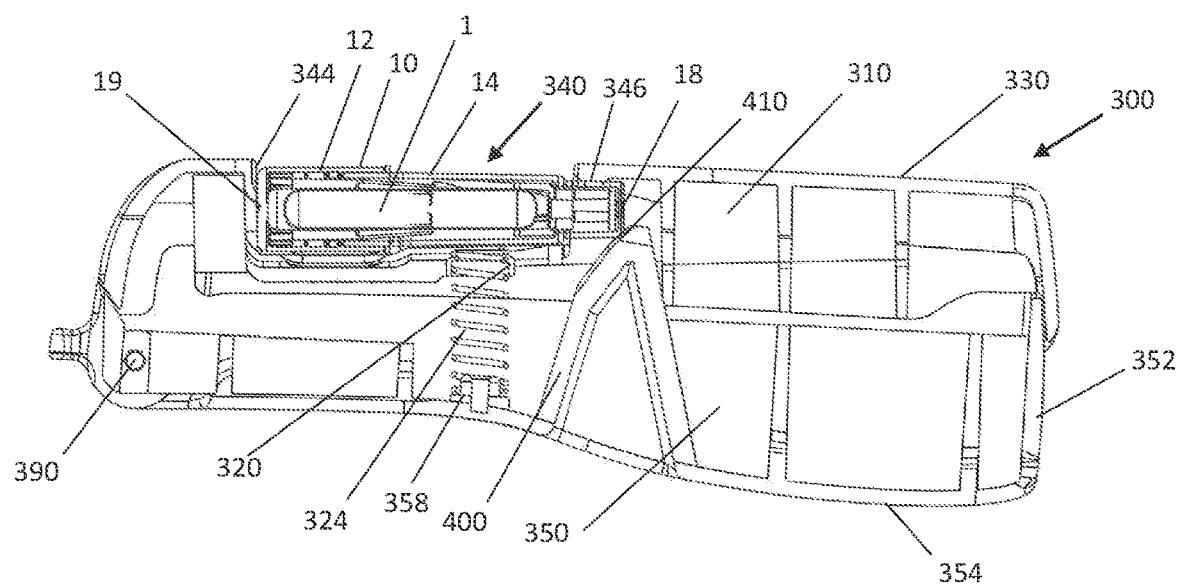
FIG. 11 depicts a sectional view of the ampoule breaker of FIG. 1 taken along section line 11-11 in FIG. 10.

FIG. 11 is a sectional view of ampoule breaker 300 taken along section line 11-11 in FIG. 10. The state shown in FIG. 11 is referred to as a rest position. As stated above, biological indicator 10 is located in receiving area 340 such that upper end 19 of biological indicator 10 contacts end wall 344 of receiving area 340. A spring 324 is located between a spring receiver 320 on main body 310 and a spring base 358 on pivoting body 350. Spring 324, or some other urging member, pushes pivoting body 350 and main body 310 away from each other. An angled surface support 400 extends upward from pivoting body 350 and has an angled surface 410 that is at a positive angle relative to end wall 344 of receiving area 340. As pivot handle 352 and main handle 330 are pressed towards each other against the force of spring 324, pivoting body 350 rotates around pin 390 at a main pivot point and angled surface 410 moves upward toward main body 310. As angled surface 410 moves toward main body 310, angled surface 410 presses on lower end 18 of biological indicator 10 and pushes lower end 18 toward end wall 344 of receiving area 340, reducing the overall length of biological indicator 10 and breaking ampoule 1. This compressed position is referred to as a biological indicator compressing position. Upward movement of lower end 18 of biological indicator 10 is prevented by an upper stop 346 of receiving area 340.

Figure 12:
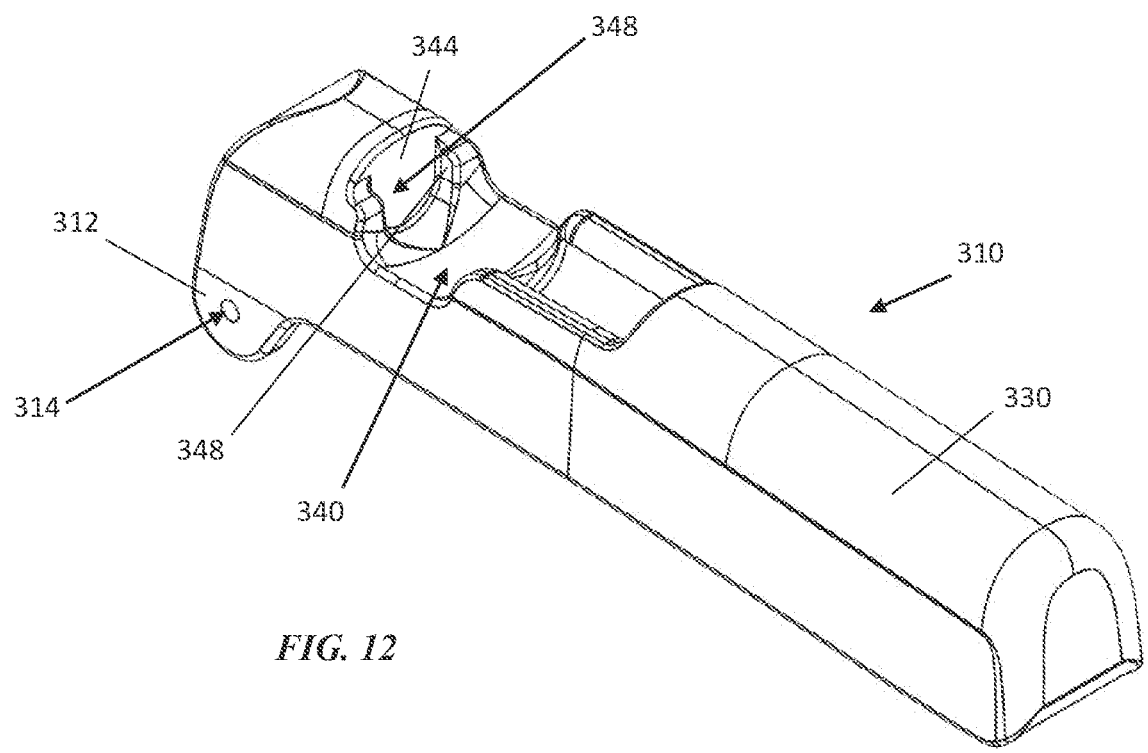
FIG. 12 depicts a perspective view of a main body of the ampoule breaker of FIG. 10.
Figure 13:
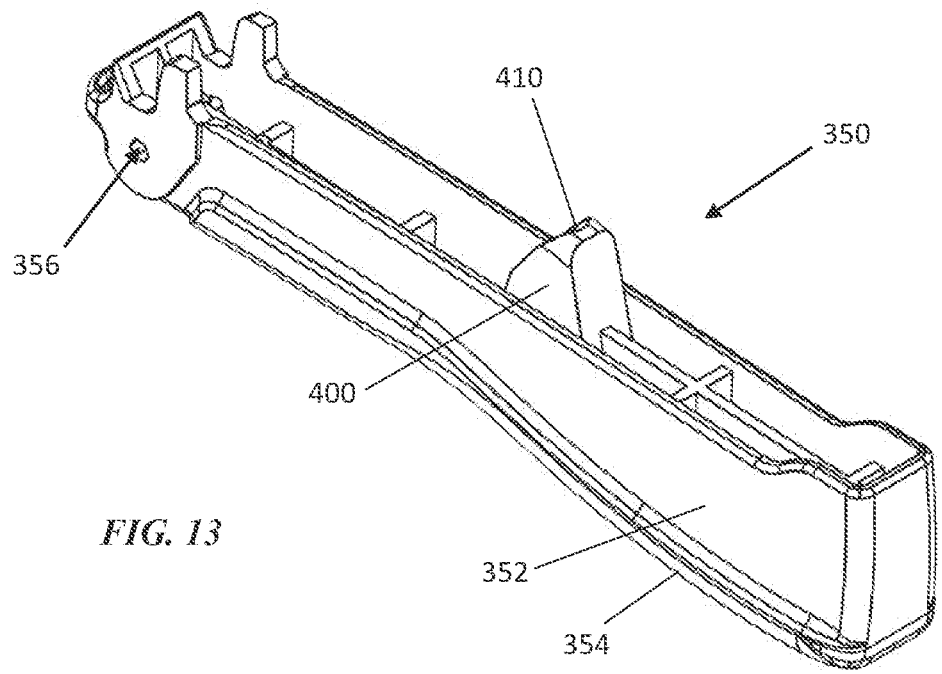
FIG. 13 depicts a perspective view of a pivoting body of the ampoule breaker of FIG. 10.
Figure 14:
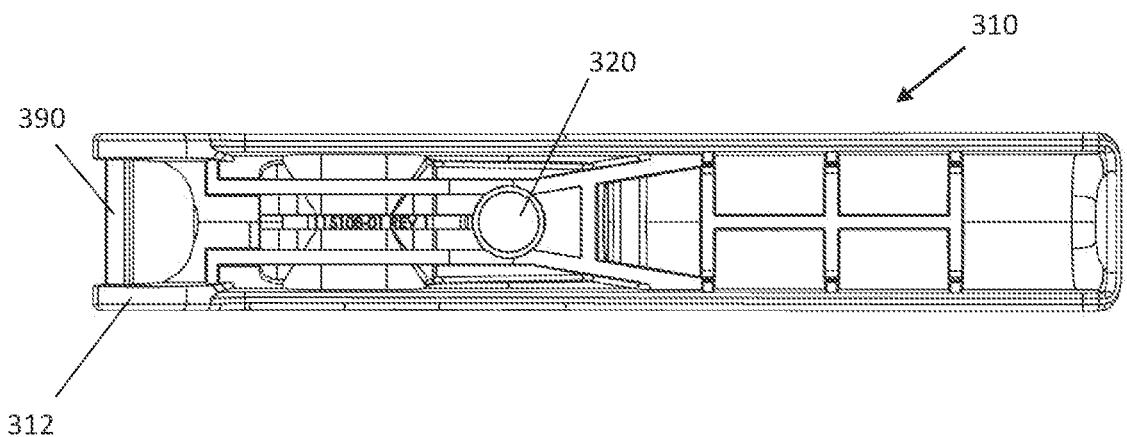
FIG. 14 depicts a bottom view of the main body of FIG. 12.

FIG. 12 is a perspective view of main body 310. As shown in FIG. 12, receiving area 340 is located in an upper portion of main body 310. As shown in FIG. 12, receiving area 340 is semi-circular in shape in the longitudinal direction of receiving area 340 to support biological indicator 10. FIG. 13 is a perspective view of pivoting body 350. As shown in FIG. 13, angled surface support 400 extends upward from pivoting body 350. Also shown in FIG. 13 is a hole 356 that receives pin 390. FIG. 14 is a bottom view of main body 310 and shows spring receiver 320.

Figure 16:
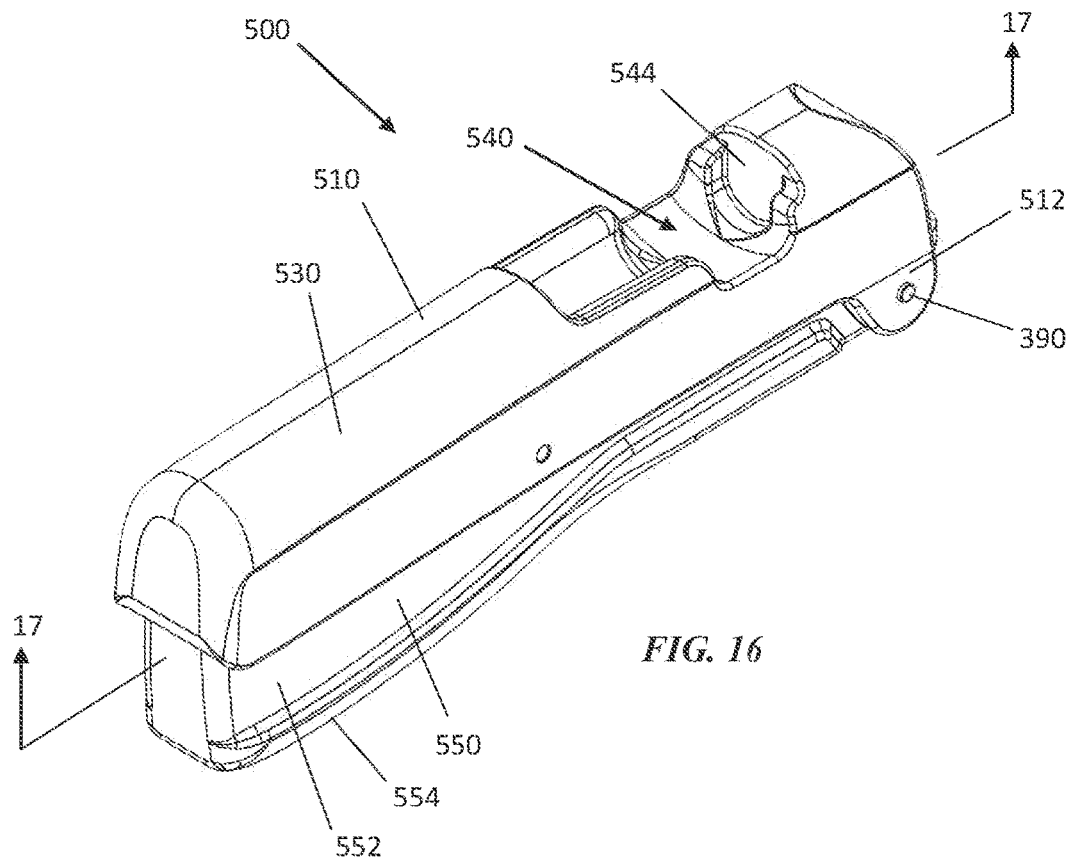
FIG. 16 depicts a perspective view of an exemplary ampoule breaker.

FIG. 16 shows an exemplary ampoule breaker 500 that is used for breaking an ampoule inside biological indicator 10. Ampoule breaker 500 has a main body 510 and a pivoting body 550. Pivoting body 550 is attached to main body 510 at a pivot point by a pin 390 at a main pivot point. Main body 510 has a hole 514 in each of two connection portions 512 that extend downward from main body 510. Pivoting body 550 includes a pivot handle 552 that has a grip section 554 to receive fingers of a user. Main body 510 has a main handle 530 that extends substantially parallel to pivot handle 550. In use, the user grips both pivot handle 552 and main handle 530 and squeezes them towards each other. Main body 510 has a receiving area 540 located in an upper region of main body 510. Receiving area 540 is configured to receive biological indicator 10 (as shown in FIG. 10). Receiving area 540 has an end wall 544 that prevents upper end 19 of biological indicator 10 from moving when ampoule breaker 500 is operated.

Figure 17:
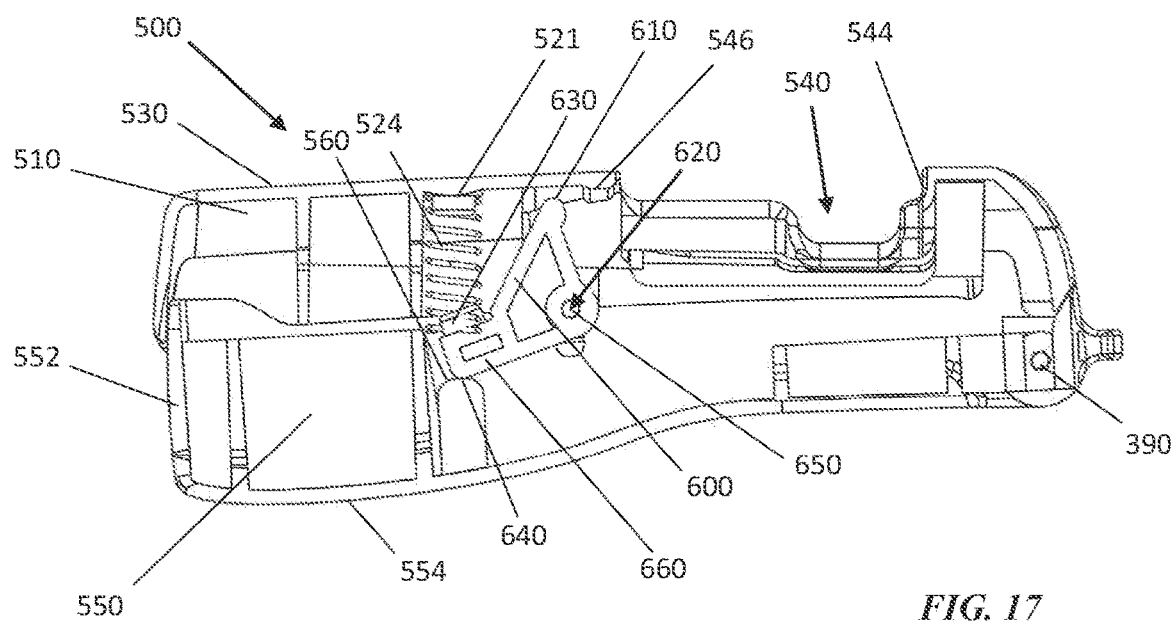
FIG. 17 depicts a sectional view of the ampoule breaker of FIG. 16 taken along section line 17-17 in FIG. 16.

FIG. 17 is a sectional view of ampoule breaker 500 taken along section line 17-17 in FIG. 16. The state shown in FIG. 17 is referred to as a rest position. Biological indicator 10 is located in receiving area 540 such that upper end 19 of biological indicator 10 contacts an end wall 544 of receiving area 540. A spring 524 is located between a spring receiver 521 on main body 510 and a spring base 630 on a compressing element 600. The state shown in FIG. 17 is referred to as the first position of compressing element 600. Compressing element 600 is attached to main body 510 at a rotation point 620 by a pin 650 such that compressing element 600 rotates relative to main body 510 around rotation point 620. Spring 524, or some other urging member, pushes pivoting body 550 and main body 510 away from each other. Compressing element 600 has a contact point 640 on a lower area of an arm 660 of compressing element 600. Contact point 640 contacts a pressing surface 560 that extends upward from pivoting body 550. As pivot handle 552 and main handle 530 are pressed towards each other against the force of spring 524, pivoting body 550 rotates around pin 390 and contact point 640 is pushed upward by pressing surface 560 against the force of spring 524. As contact point 640 moves upward toward main body 510, compressing element 600 rotates around rotation point 620 and compressing surface 610 moves toward end wall 544. When biological indicator 10 is present in receiving area 540, compressing surface 610 contacts lower end 18 of biological indicator 10 and pushes lower end 18 toward end wall 544 of receiving area 540, reducing the overall length of biological indicator 10 and breaking ampoule 1. This state is referred to as the second position. Upward movement of lower end 18 of biological indicator 10 is prevented by an upper stop 546 of receiving area 540.

Figure 18:
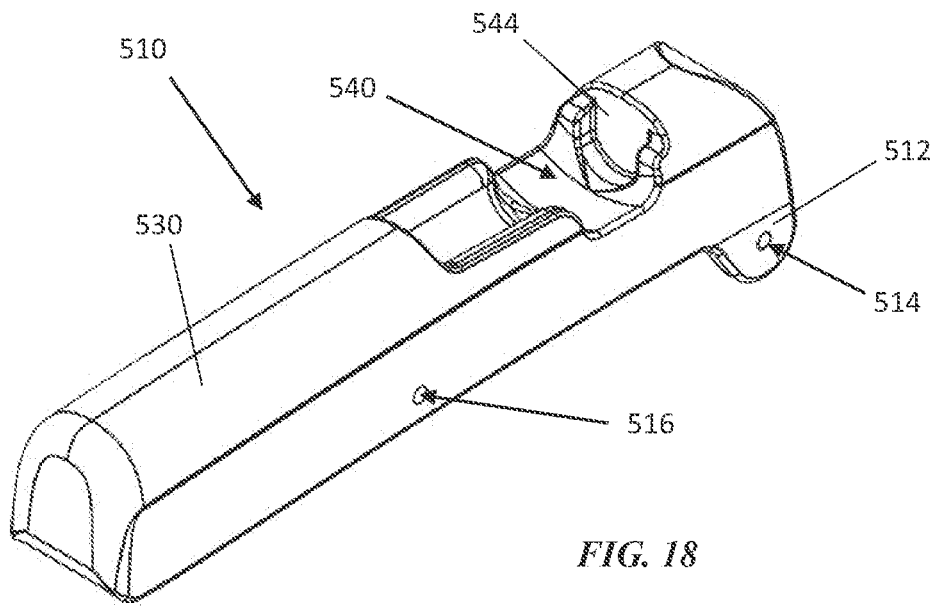
FIG. 18 depicts a perspective view of a main body of the ampoule breaker of FIG. 16.
Figure 19:
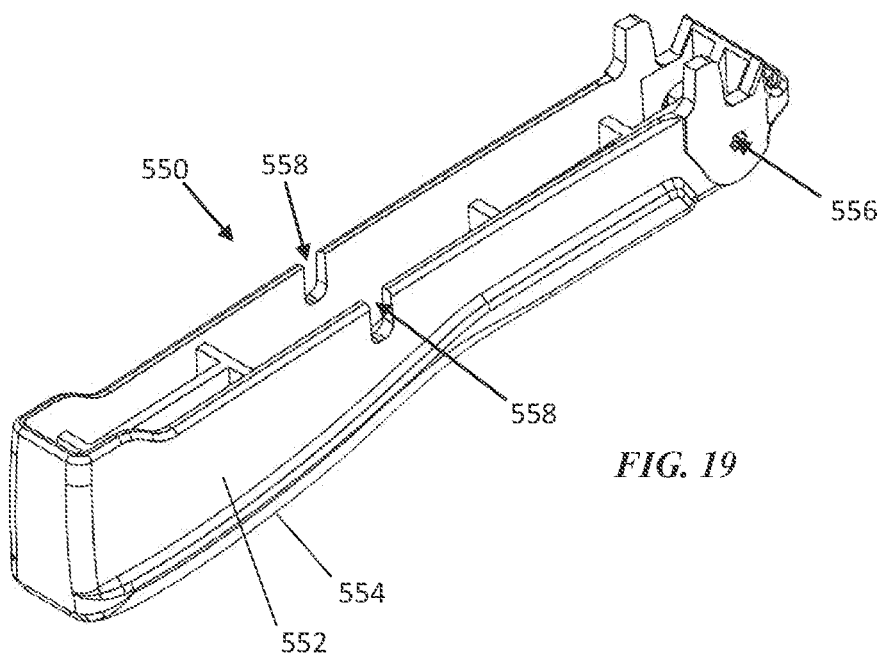
FIG. 19 depicts a perspective view of a pivoting body of the ampoule breaker of FIG. 16.
Figure 20:
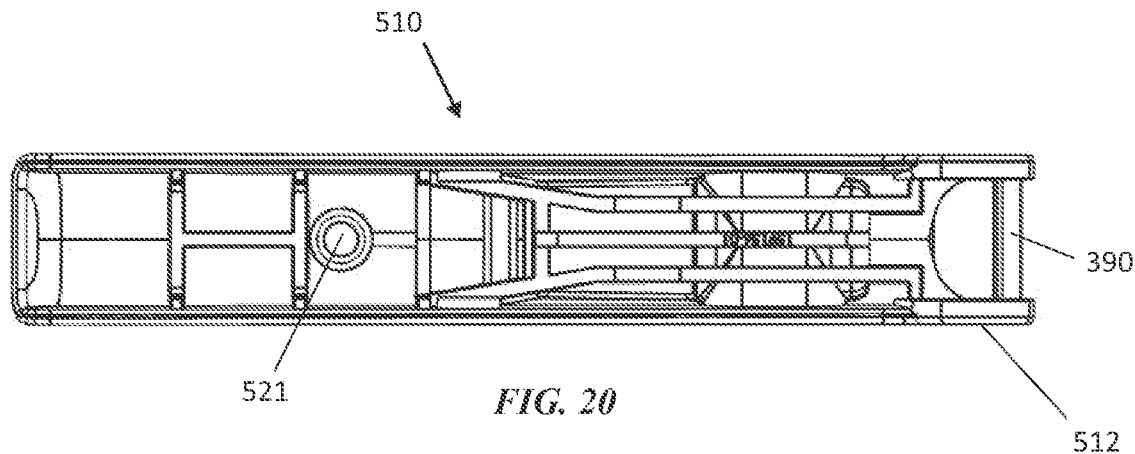
FIG. 20 depicts a bottom view of the main body of FIG. 18.

FIG. 18 is a perspective view of main body 510. As shown in FIG. 18, receiving area 540 is located in an upper portion of main body 510. As shown in FIG. 18, receiving area 540 is semi-circular in shape in the longitudinal direction of receiving area 540 to support biological indicator 10. FIG. 19 is a perspective view of pivoting body 550. As shown in FIG. 19, pivoting body 550 has two notches 558 in sidewalls of pivoting body 550. A pin extends through one hole 516, rotation point 620, and the other hole 516 to secure compressing element 600 in position. Notches 558 in pivoting body 550 allow main body 510 to move downward around pivoting body 550 without being stopped by pin 650. Also shown in FIG. 19 is a hole 556 that receives pin 390. FIG. 20 is a bottom view of main body 510 and shows spring receiver 521.

Figure 21:
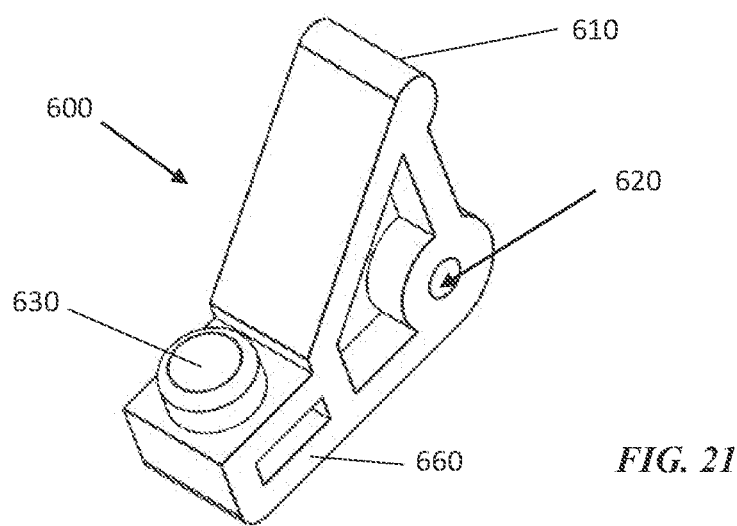
FIG. 21 depicts a perspective view of an exemplary compressing element.

FIG. 21 is a perspective view of compressing element 600 showing compressing surface 610 as rounded to facilitate compressing surface 610 sliding against lower end 18 of biological indicator 10 when compressing element rotates around rotation point 620.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of breaking an ampoule of a biological indicator, the method comprising:
   disposing the ampoule of the biological indicator in a breaking device, the breaking device comprising:
   a main body;
   a pivoting body attached to the main body at a main pivot point;
   a receiving area in the main body configured to receive the ampoule of the biological indicator;
   a pressing surface inside the pivoting body; and
   a compressing element including a compressing surface, the compressing surface being operable between a first position and a second position located in the receiving area;
   pivoting the pivoting body from a rest position to a compressed position;
   urging the compressing element against the pressing surface with an urging member located between the main body and the compressing element; and
   breaking the ampoule of the biological indicator.

2. The method of claim 1, in which the step of pivoting the pivoting body comprises moving the pressing surface toward the main body.

3. The method of claim 2, in which the step of breaking the ampoule comprises moving the compressing surface from the first position to the second position.

4. The method of claim 3, in which the compressing element pivots about a compression pivot point as the compressing surface moves between the first position and the second position.

5. The method of claim 4, further comprising receiving the ampoule of the biological indicator between an end wall of the receiving area and the compressing surface.

6. The method of claim 5, in which the compressing surface moves toward the end wall when the compressing surface moves from the first position to the second position.

7. The method of claim 6, in which the receiving area is open on at least one side.

8. The method of claim 7, in which a portion of one of the pivoting body and the main body extends over the other of the pivoting body and the main body.

9. A method of breaking an ampoule of a biological indicator, the method comprising:
   disposing the biological indicator in a breaking device, the breaking device comprising:
   a main body;
   a pivoting body attached to the main body at a main pivot point, wherein a portion of one of the pivoting body and the main body extends over the other of the pivoting body and the main body;
   a receiving area in the main body configured to receive the ampoule of the biological indicator, wherein the receiving area is open on at least one side;
   a pressing surface inside the pivoting body;
   a compressing element including a compressing surface, the compressing surface being operable between a first position and a second position located in the receiving area, wherein the compressing element pivots about a compression pivot point as the compressing surface moves between the first position and the second position;
   pivoting the pivoting body from a rest position to a compressed position by moving the pressing surface toward the main body;
   urging the compressing element against the pressing surface with an urging member located between the main body and the compressing element;
   receiving the ampoule of the biological indicator between an end wall of the receiving area and the compressing surface; and
   breaking the ampoule by moving the compressing surface from the first position to the second position, wherein the compressing surface moves toward the end wall when the compressing surface moves from the first position to the second position.

10. A device for breaking an ampoule of a biological indicator, the device comprising:
    a main body;
    a pivoting body attached to the main body at a main pivot point;
    a receiving area in the main body configured to receive the ampoule of the biological indicator;
    a pressing surface inside the pivoting body; and
    a compressing element including a compressing surface, the compressing surface being operable between a first position and a second position in receiving area, wherein the compressing element is attached to the pivoting body by a compressing pivot point, wherein an urging member located between the main body and the compressing element urges the compressing element to contact the pressing surface.

11. The device of claim 10, in which the compressing surface is a portion of the compressing element.

12. The device of claim 10, in which the receiving area has an end wall, and the receiving area is configured to receive the ampoule of the biological indicator between the end wall and the compressing surface.

13. A device for breaking an ampoule of a biological indicator, the device comprising:
    a main body;
    a pivoting body attached to the main body at a main pivot point;
    a receiving area in the main body, wherein the receiving area has an end wall, and the receiving area is configured to receive the ampoule of the biological indicator between the end wall and the compressing surface;
    a pressing surface inside the pivoting body; and
    a compressing element including a compressing surface, the compressing surface being operable between a first position and a second position located in the receiving area,
    wherein the compressing element is attached to the pivoting body by a compressing pivot point and an urging member located between the main body and the compressing element urges the compressing element to contact the pressing surface.

* * * * *